United States Patent [19]

Komoto et al.

[11] Patent Number: 4,584,311

[45] Date of Patent: Apr. 22, 1986

[54] MICROBIOCIDAL 1-[1-(ALKOXYPHENYL)VINYL]-1H-IMIDAZOLES

[75] Inventors: Nobuo Komoto, Mitaka; Kiyoshi Arai; Setsuko Hirose, both of Yokohama, all of Japan

[73] Assignee: Mitsui Toatsu Chemicals, Inc., Tokyo, Japan

[21] Appl. No.: 689,063

[22] Filed: Jan. 7, 1985

[30] Foreign Application Priority Data

Jan. 9, 1984 [JP] Japan ................................. 59-823

[51] Int. Cl.⁴ .................... A01N 43/50; C07D 233/60
[52] U.S. Cl. .................................... 514/399; 548/335
[58] Field of Search ................ 548/335; 514/396, 399

[56] References Cited

U.S. PATENT DOCUMENTS 4,328,348  5/1982  Ogata et al. ......................... 548/335
4,459,412  7/1984  Ogata .................................. 548/335

Primary Examiner—Richard A. Schwartz
Assistant Examiner—Kurt G. Briscoe
Attorney, Agent, or Firm—Fisher, Christen & Sabol

[57] ABSTRACT

Imidazole derivatives of general formula (I) and acid addition salts thereof, which are useful as industrial microbicides.

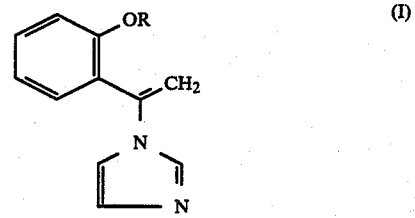

wherein
R represents a linear or branched alkyl group having 6 to 9 carbon atoms.

7 Claims, No Drawings

MICROBIOCIDAL 1-[1-(ALKOXYPHENYL)VINYL]-1H-IMIDAZOLES

This invention relates to imidazole derivatives and their acid addition salts and to industrial microbicides comprising them as active ingredients.

Inorganic or organic compounds of heavy metals such as mercury, tin and copper have mainly been used widely as industrial microbicides because of their outstanding microbicidal effect. Since, however, these compounds have strong toxicity to humans and other animals, their use gives rise to a problem. Moreover, they are likely to remain in products in which they are used, and have a risk of causing secondary troubles. Furthermore, they involve environmental pollution when present in waste liquors and wastes. Non-metallic fungicides which came into use in place of the above compounds do not have sufficient fungicidal effects and have been found to be effective only against limited kinds of fungi. Furthermore, these compounds frequently deteriorate industrial materials or products or degrade their qualities.

For example, benzimidazole-type compounds considered to be best among the non-metallic microbicides exhibit antimicrobial activity comparable to that of organic mercury agents against fungi of the genera Aspergillus, Penicillium, Trichoderma, etc. which occur in, and deteriorate paints, pastes, wood and bamboo products, leathers, etc., but have the defect of exhibiting no appreciable effect against fungi of the genera Alternaria, Mucro, etc. which occur in surfaces coated with emulsion paints, artificial leather, wall cloths, etc. when used in practical concentrations (100 to 500 ppm).

It is an object of this invention therefore to provide an industrial microbicide which has excellent microbicidal activity and can accurately control a wide range of fungi which occur in, and deteriorate, industrial materials and products.

In order to achieve this object, the present inventors synthesized numerous imidazole derivatives and subjected them to antimicrobial tests. These efforts have led to the discovery that imidazole derivatives represented by the following general formula (I)

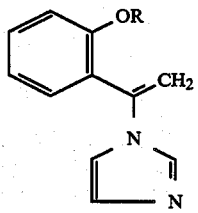

(I)

wherein
R represents a linear or branched alkyl group having 6 to 9 carbon atoms,
and acid addition salts thereof show very good microbical activity and a wide antimicrobial spectrum against many fungi which cause biodeterioration of industrial materials or products.

The compounds of this invention are novel substances not described in the prior literature. U.S. Pat. No. 4,328,348 discloses imidazole derivatives of general formula (I) in which R is an alkyl group having 1 to 5 carbon atoms, i.e. methyl, ethyl, propyl, isopropyl, butyl, sec-butyl, pentyl or isopentyl, and their acid addition salts which are similar to the compounds of this invention. This patent document shows examples of in vitro antimycotic tests (minimum growth inhibition concentrations against *Aspergillus fumigates, Candida albicans* and *Trichophyton asteroides* which are Eumycetes infecting living creatures) and an example of a control test on gray mold (Botrytis Cinerea), and suggests that these compounds are effective as antimycotic agents for humans and other animals or as agricultural fungicides. The patent document, however, does not even suggest whether these compounds have microbicidal activity against microbes which cause biodeterioration of industrial materials or products.

According to this invention, there are provided imidazole derivatives of general formula (I) wherein R represents a linear or branched alkyl group having 6 to 9 carbon atoms and acid addition salts thereof which are highly active and useful industrial microbicides.

The compounds of this invention have unique microbicidal activity against microbe which are sources of biodeterioration of industrial materials or products over other compounds having alkyl chains. They have unexpected and outstanding antimicrobial activity and a wide antimicrobial spectrum as compared with the aforesaid known compounds of general formula (I) in which R is an alkyl group having 1 to 5 carbon atoms, or with compounds of general formula (I) in which R is an alkyl group having 10 or more carbon atoms. The compounds of this invention show especially outstanding strong microbicidal activity against Eumycetes such as *Cladosporium herbarum* which degrades paints, latices and rubber materials, *Chaetomium globosum* which degrades fibers, plastics, paper and pulp, and *Aureobasidium pullulans* which degrades wood, paints, and packaging materials (aluminum foils, plastics, paper, etc.). The compounds of this invention have far stronger microbicidal activity than 2-(4-thiazolyl)benzimidazole (TBZ for short) which is a typical benzimidazole-type industrial microbicide now on the market. The compounds of this invention also show an outstanding effect against microbes such as those of the genus Alternaria for the control of which the development of effective chemicals has been desired. These compounds also have superior stability to light, heat and oxidation.

As stated above, the compounds of this invention have excellent properties as industrial microbicides and can be used in a wide range of fields, for example general industrial products such as paints, pastes, wooden or bamboo products, leathers, fibers, wall finishing materials, resin emulsions, adhesives, cooling lubricants and biodegradable plastic products.

The compounds of formula (I) in accordance with this invention are synthesized in accordance with the following reaction scheme.

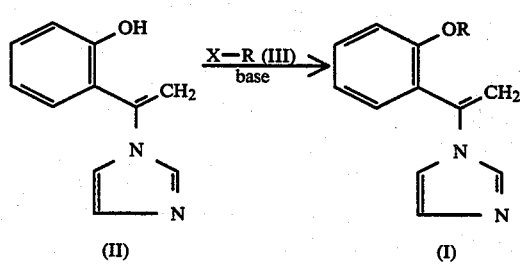

In the above scheme, X represents halogen or an ester residue (e.g., tosyl), and R represents a linear or branched alkyl group having 6 to 9 carbon atoms. Specifically, the compounds of this invention can be easily obtained by a method which comprises reacting a intermediate (II) which can be easily synthesized from o-hydroxyacetophenone and N,N'-thionyldimidazole, with a compound (III). Examples of the base used in the reaction include sodium hydroxide, poassium hydroxide, sodium carbonate, potassium carbonate, sodium hydrogen carbonate, potassium hydrogen carbonate, sodium hydride, potassium hydride, sodium alcoholate, sodium amide, pyridine and triethylamine. The reaction is carried out at room temperature or an elevated temperature in a suitable inert solvent such as dimethylformamide, benzene, toluene, methanol, chloroform, dimethylsulfoxide or tetrahydrofuran. The reaction temperature can be properly selected within the range of 15° to 150° C.

As required, the resulting product (I) can be converted to its acid addition salt. Acids capable of forming such salts include, for example, organic acids such as acetic acid, citric acid, tartaric acid, malic acid, succinic acid, oxalic acid and maleic acid, and inorganic acids such as hydrohalic acids, sulfuric acid, nitric acid and phosphoric acid.

The synthesis of 1-[1-(2-hydroxyphenyl)vinyl]-1H-imidazole, the intermediate for producing the compounds of this invention, is shown by the following referential example.

REFERENTIAL EXAMPLE

Thionyl chloride (26.2 g; 0.22 mole) was gradually added dropwise to a solution composed of 60 g (0.88 mole) of imidazole and 300 ml of dry methylene chloride while maintaining the solution at 20° C. The mixture was stirred further for 10 minutes, and while maintaining the temperature of the solution at about 20° C., 22 g (0.16 mole) of o-hydroxyacetophenone was gradually added. Stirring was continued for 30 minutes at room temperature, and the solvent was removed at less than 40° C. under reduced pressure. To the residue was gradually added under ice cooling an aqueous solution of potassium carbonate ($K_2CO_3$ 45.5 g, 0.33 mole; water 140 ml). The solid obtained was collected by filtration, and then fully washed with water and further with acetone to give 25.3 g (yield 84.2%) of a pale yellow solid (II) (mp. 151°–152° C.).

NMR spectrum $\delta_{TMS}^{DMSO-D6}$(ppm): 5.07(1H, S), 5.52(1H, S), 6.87–7.23(6H, m), 7.59(1H, S).

The compounds of this invention are used normally in the form of a formulation held on a carrier, for example in the form of an oil solution, an emulsifiable concentrate, a paste, a dust, a wettable power or an aerosol. Examples of the carrier include inorganic solid carriers such as clay, talc, bentonite, kaolin, silicic anhydride and calcium carbonate; organic solvent-type carriers such as benzene, toluene, xylene, kerosene, chloroform, dichloroethane, acetone, methyl ethyl ketone, dioxane, tetrahydrofuran, methanol, propanol, dimethylformamide and dimethyl sulfoxide; and gaseous carriers such as dimethyl ether and flon gas. As required, ionic or non-ionic surface-active agents and polymeric compounds such as polyvinyl acetate and methyl cellulose may be used together as adjuvants for increasing the formulation effect. When the compounds of this invention are to be applied as microbicides, they may be used in combination with other antibacterial and antifungal agents or with agricultural chemicals such as insecticides, fungicides, miticides, antiviral agents, herbicides and plant growth regulators.

The following examples illustrate the present invention more specifically. It should be understood that the invention is in no way limited to these examples.

EXAMPLE 1

This example illustrates the production of 1-[1-(2-n-hexyloxyphenyl)vinyl]-1H-imidazole The solid (II) obtained in Referential Example given hereinabove (2.5 g; 0.013 mole) was dissolved in 10 ml of dry dimethylformamide, and 0.7 g (0.018 mole) of 60% sodium hydride (as a suspension in a mineral oil) was added under ice cooling. The mixture was stirred. Five minutes later, 1.6 g (0.013 mole) of 1-chlorohexane was added, and the mixture was stirred at 40° to 50° C. for 5 hours. Ice water was added to the reaction mixture, and it was extracted with toluene. The organic layer was washed with water and dried over anhydrous sodium sulfate. Toluene was evaporated, and the residue was purified by chromatography on a column of silica gel. The column was eluted with 30% ethyl acetate/n-hexane. The eluates were concentrated to give 3.30 g (yield 92%) of an oily substance (1).

$[n]_D^{21.2}$: 1.5437.

NMR $\delta_{TMS}^{CDCl3}$(ppm): 0.80–0.92(3H, m); 1.24–1.56(8H, m); 3.80(2H, t, J=4 Hz); 5.05(1H. s); 5.32(1H, s); 6.80–7.00(4H, m); 7.14–7.44(3H, m).

HCl-ethanol was added to 1 g of the resulting oily substance (1), and the mixture was concentrated. The residue was recrystallized from methanol-acetic acid to give 0.92 g of the hydrochloride of the oily substance (1). Melting point 107°–110° C.

EXAMPLES 2-7

The products given in Table 1 were synthesized in the same way as in Example 1.

TABLE 1

| Example | R | Type of salt | Physical constant | NMR $\delta_{TMS}^{CDCl3}$ (ppm) |
|---|---|---|---|---|
| 2 | —(CH$_2$)$_6$CH$_3$ | — | $[n]_D^{21.3}$ 1.5382 | 0.81–0.93(3H, m); 1.24–1.56(10H, m); 3.81(2H, t, J=6Hz); 5.07(1H, S); 5.36(1H, S); 6.82–7.01(4H, m); 7.22–7.47(3H, m) |
| 3 | —(CH$_2$)$_7$CH$_3$ | — | $[n]_D^{21.4}$ 1.5387 | 0.82–0.93(3H, m); 1.25–1.56(12H, m); 3.79(2H, t, J=6Hz); 5.04(1H, S); 5.32(1H, S); 6.77–6.96(4H, m); 7.16–7.40(3H, m) |
| 4 | —(CH$_2$)$_7$CH$_3$ | HCl | m.p. 108–111° C. | Same as in Example 3 |
| 5 | CH$_3$<br>\|<br>—CH—(CH$_2$)$_5$CH$_3$ | — | $[n]_D^{21.3}$ 1.5332 | 0.80–0.92(3H, m); 1.07(3H, d, J=7Hz); 1.24–1.54(10H, m); 4.14–4.38(1H, m); 5.06(1H, S); 5.35(1H, S); 6.80–7.02(4H, m); 7.22–7.48(3H, m) |

TABLE 1-continued

| Example | R | Type of salt | Physical constant | NMR $\delta_{TMS}^{CDCl_3}$ (ppm) |
|---|---|---|---|---|
| 6 | —(CH$_2$)$_8$CH$_3$ | — | $[n]_D^{21.3}$ 1.5245 | 0.81–0.94(3H, m); 1.25–1.56(14H, m); 3.82(2H, t, J=6Hz); 5.08(1H, S); 5.36(1H, S); 6.83–7.02(4H, m); 7.23–7.48(3H, m) |
| 7 | —(CH$_2$)$_8$CH$_3$ | HCl | m.p. 99–101° C. | Same as in Example 6 |

EXAMPLE 8

This example illustrates the microbicidal activity of the compounds of this invention. Each of the compounds of this invention, the known compounds of formula (I) in which R is an alkyl group having 1 to 5 carbon atoms or 3-chlorobenzyl, commercial TBZ, and reference compounds of formula (I) in which R is an alkyl group having 10 or 12 carbon atoms was incorporated in a potato dextrose agar medium (PDA medium) in a concentration range of 0.03 to 100 ppm. The medium was well stirred, and poured into a Petri dish to form an agar plate. After the agar solidified, a pure culture of each of the test organisms tabulated below (as a suspension mainly of conidiospores, excepting *Alternaria alternata*) The organism was cultivated at 24° C. for 7 days, and the minimum concentration of the test compound in the medium at which the inoculated organism did not grow was determined and recorded in Table 2 as the minimum inhibitory concentration (MIC).

| Organism | Abbreviation |
|---|---|
| *Aspergillus niger* | A.n. |
| *Penicillium citrinum* | P.c. |
| *Cladosporium herbarum* | C.h. |
| *Chaetomium globosum* | C.g. |
| *Trichoderma viride* | T.v. |
| *Aureobasidium pullulans* | A.p. |
| *Gibberella fujikuroi* | G.f. |
| *Alternaria alternata* | A.a. |

TABLE 2

Microbicidal activity (MIC, ppm)

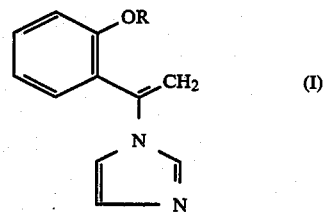

(I)

| | R | A.n. | P.c. | C.h. | C.g. | T.v. | A.p. | G.f. | A.a. |
|---|---|---|---|---|---|---|---|---|---|
| Known compound | | | | | | | | | |
| i | —CH$_3$ | 50 | 50< | 50 | 50< | 50< | 50< | 50< | 50< |
| ii | —CH$_2$CH$_3$ | 10 | 50 | 50 | 50 | 50< | 50 | 50 | 50 |
| iii | —CHCH$_3$ (CH$_3$) | 10 | 50 | 50 | 50 | 50< | 10 | 50 | 10 |
| iv | —(CH$_2$)$_3$CH$_3$ | 2 | 2 | 2 | 10 | 50 | 2 | 10 | 2 |
| v | —(CH$_2$)$_4$CH$_3$ | 0.4 | 2 | 2 | 10 | 50 | 2 | 2 | 2 |
| vi | —CH$_2$CH$_2$CHCH$_3$ (CH$_3$) | 2 | 2 | 10 | 10 | 50 | 10 | 2 | 2 |
| vii | —CH$_2$-C$_6$H$_4$Cl | 2 | 2 | 10 | 10 | 50 | 2 | 10 | 10 |
| TBZ | — | 2 | 0.4 | 2 | 2 | 2 | 0.4 | 2 | 100< |
| Compound of this invention | | | | | | | | | |
| 1 | —(CH$_2$)$_5$CH$_3$ | 0.1 | 0.1 | 0.2 | 0.4 | 10 | 0.4 | 0.4 | 0.4 |
| 2 | —(CH$_2$)$_6$CH$_3$ | 0.2 | 0.1 | 0.05 | 0.4 | 10 | 0.2 | 0.4 | 0.4 |
| 3 | —(CH$_2$)$_7$CH$_3$ | 0.2 | 0.05 | 0.03 | 0.2 | 2 | 0.05 | 0.4 | 0.4 |
| 6 | —(CH$_2$)$_8$CH$_3$ | 0.1 | 0.05 | 0.1 | 0.4 | 10 | 0.2 | 0.4 | 0.4 |
| Reference compound | | | | | | | | | |
| i | —(CH$_2$)$_9$CH$_3$ | 2 | 2 | 0.4 | 2 | 100< | 10 | 10 | 2 |
| ii | —(CH$_2$)$_{11}$CH$_3$ | 100< | 100< | 100< | 100< | 100< | 100< | 100< | 100< |

What is claimed is:

1. An imidazole derivative represented by the formula:

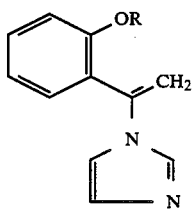

(I)

wherein R represents a linear or branched alkyl group having 6 to 9 carbon atoms, or an acid addition salt thereof.

2. The imidazole derivatives as claimed in claim 1 wherein R is —(CH$_2$)$_5$CH$_3$, —(CH$_2$)$_6$CH$_3$, —(CH$_2$)$_7$CH$_3$,

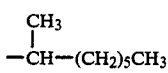

or —(CH$_2$)$_8$CH$_3$.

3. The imidazole derivative as claimed in claim 1 wherein the imidazole derivative is the acid addition salt of acetic acid, citric acid, tartaric acid, malic acid, succinic acid, oxalic acid, maleic acid, a hydrohalic acid, sulfuric acid, nitric acid or phosphoric acid.

4. An industrial microbicidal composition comprising (a), as an active ingredient, a microbicidally effective amount of an imidazole derivative represented by the formula:

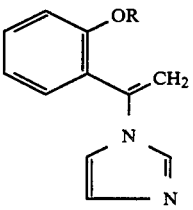

(I)

wherein R represents a linear or branched alkyl group having 6 to 9 carbon atoms, or an acid addition salt thereof, and (b) a carrier.

5. The industrial microbicidal composition as claimed in claim 4 wherein R is —(CH$_2$)$_5$CH$_3$, —(CH$_2$)$_6$CH$_3$, —(CH$_2$)$_7$CH$_3$,

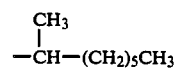

or —(CH$_2$)$_8$CH$_3$.

6. The industrial microbicidal composition as claimed in claim 4 wherein the imidazole derivative is the acid addition salt of acetic acid, citric acid, tartaric acid, malic acid, succinic acid, oxalic acid, maleic acid, a hydrohalic acid, sulfuric acid, nitric acid or phosphoric acid.

7. The industrial microbicidal composition as claimed in claim 4 wherein the carrier is an inorganic solid carrier, an organic solvent-type carrier or a gaseous carrier.

* * * * *